United States Patent [19]

Holtkamp, Sr.

[11] Patent Number: Plant 6,932

[45] Date of Patent: Jul. 18, 1989

[54] AFRICAN VIOLET PLANT NAMED IMPROVED MANITOBA

[76] Inventor: Reinhold Holtkamp, Sr., Werther Strasse 112, D4294 Isselburg, Fed. Rep. of Germany

[21] Appl. No.: 192,682

[22] Filed: May 10, 1988

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new and distinct cultivar of African violet named Improved Manitoba characterized by its large, single, occasionally semi-double, violet-blue flowers with partly fine white edges; strong, upright flower stems that curve slightly toward the center to form a compact bouquet above the leaves; medium green oval to spear-shaped, slightly serrated leaves; profuse flowering, vigorous growth habit, flowering 10–11 weeks after potting, and its long lasting and non-dropping flowers.

1 Drawing Sheet

The present invention comprises a new and distinct cultivar of African violet plant, botanically known as *Saintpaulia ionantha,* and hereinafter referred to by the cultivar name Improved Manitoba.

The new cultivar was referred to during the breeding and selection process by the designation H 77/27 and is a product of a planned breeding program. The basic objective of the breeding program was to create a new African violet cultivar improving certain characteristics of the cultivar Manitoba, disclosed in my U.S. Plant Pat. No. 4,550 granted in 1980.

The new cultivar was originated from a cross made by me in the controlled breeding program in Haffen, Federal Republic of Germany. The female, or seed parent was a cultivar designated D 198/5. The male, or pollen parent was a cultivar designated GG 18 Light Blue Star.

Improved Manitoba was discovered and selected by me in as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Improved Manitoba has not been observed under all possible environmental conditions. The phenotype may vary significantly with variations in environment such as temperature, light intensity and day length. The following observations, measurements and values describe the new cultivar as grown in a 10 cm pot in Haffen, West Germany and Nashville, Tenn. under greenhouse conditions which closely approximate those generally used in commercial practice.

The following traits have been repeatedly observed and are determined to be basic characteristics of Improved Manitoba, which in combination distinguish this African violet as a new and distinct cultivar:

(1) Strong, upright flower stems curving slightly toward the center.

(2) Large, single, occasionally semi-double, violet-blue flowers with partly fine white edges.

(3) Each plant carries 6–8 and more upright flower stems each of which carries 8–10 and more flowers.

(4) Long lasting, non-dropping flowers.

(5) Vigorous grower.

(6) Plant saleable 10 to 11 weeks after potting.

(7) Seed capsules push slightly through.

(8) Oval to spear-shaped, slightly serrated, medium green leaves.

(9) After maturity the flowers dry off, and remain on the peduncle without becoming infected by botrytis.

The new cultivar is most similar to, and was specifically intended to improve upon the characteristics of, my previously patented cultivar, Manitoba. In comparison to Manitoba, the new cultivar is principally distinguished by its darker and occasionally semi-double flower, partly fine white edges, and by its brighter green leaves. In contrast to Manitoba, the new cultivar has long-lasting flowers which do not drop even under stress conditions. The new cultivar is also similar in growth habit and flower shape to Barbados which has the same parents.

The accompanying color photographic drawing shows a typical specimen plant of the new cultivar. The colors appearing in the photograph are as true as possible with color illustrations of this type.

In the following description, color references are made to The Royal Horticultural Society Colour Chart (RHS), except where general colors of ordinary significance are referred to. Color values were taken under natural sunlight conditions at approximately 2 p.m. in Nashville, Tenn.

Botanical classification: *Saintpaulia ionantha,* Ramt., c.v. Improved Manitoba.

Parentage:

*Male parent.*—GG 18 Light Blue Star.

*Female parent.*—D 198/5 Blue Single.

Propagation: The new cultivar holds its distinguishing characteristics through successive propagations by leaf cuttings.

Plant: From 10 cm to 12 cm tall when grown in pots, and approximately 25–30 cm in diameter when fully grown.

*Leaves.*—General form: Oval to spear-shaped. Diameter: 60–75 mm wide and 75–90 mm long. Texture: Velvety and soft. Aspect: Hairy, slightly shiny, slightly serrated. Veins: Upperside: well visible; underside: very well pronounced, light green, shiny. Color (upperside):

Yellow-Green Group 147 between A and B. Color (underside): Greyed-Green Group 193 B. Petiole: Strong upright, purplish green, hairy.

*Flowers.*—Buds: Ball-shaped, 8–9 mm just before opening, violet-blue. Sepals: Five (5). Color: Brownish green. Calyx: Shape: Funnel-shaped. Aspect: Spear-shaped, hairy. Peduncle: Character: Strong upright, hairy. Color: Purplish brown.

*Individual flowers.*—Size: 45–55 mm. Shape: Single violet-shaped (3 large, 2 small petals), occasionally semi-double having up to 5 more petals. Color (upperside): Violet-Blue Group 93 between B and C. Under cooler temperatures and more intensive lighting, the blue tends to intensify. Color (underside): Violet-Blue Group 93 D. Borne: Each flower stem carries 8–10 and more flowers on strong, upright peduncles that are free standing above the leaves, thereby forming a compact bouquet. Flowering Habit: Flowers 10–11 weeks after potting.

*Reproductive organs.*—Stamens: Two (2). Anthers: 2 composed of 4 anther cells, seed capsule pushes slightly through. Filaments: Yellowish green with blue touch on edges, 4–5 mm long. Pollen color: Yellow Group 7. Styles: 7–8 mm long, purplish blue, base of ovary light green and hairy.

*Roots.*—Normally developed, white when young, turning slightly brownish when older.

Disease resistance: Good.

General observations: Improved Manitoba is a very attractive, vigorous large grower with medium green, oval to spear-shaped, slightly serrated leaves. A tight bouquet of flowers free standing above the leaves develops after approximately 10–11 weeks. Each of the 6–8 and more strong flower stems carries 8–10 and more large, single, occasionally semi-double, violet-blue flowers with partly fine white edges. The center and the two small petals have a somewhat darker color. The flowers are long-lasting and non-dropping and the seed capsules push slightly through.

I claim:

1. A new and distinct cultivar of African violet named Improved Manitoba, as described and illustrated, and particularly characterized by its large, single, occasionally semi-double, violet-blue flowers with partly fine white edges; strong, upright flower stems that curve slightly toward the center to form a compact bouquet above the leaves; medium green oval to spear-shaped, slightly serrated leaves; profuse flowering, vigorous growth habit, flowering 10–11 weeks after potting, and its long lasting and non-dropping flowers.

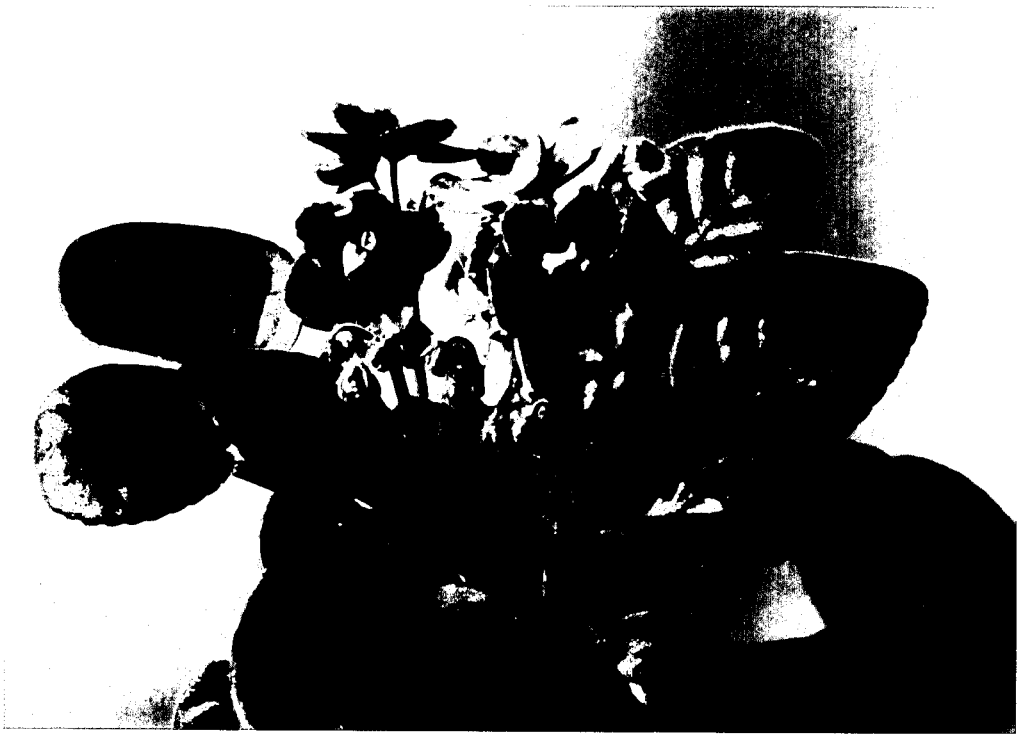

* * * * *